US006033858A

United States Patent [19]
Bastian

[11] Patent Number: 6,033,858
[45] Date of Patent: Mar. 7, 2000

[54] DETECTION OF TRANSMISSIBLE SPONGIFORM ENCEPHALOPATHIES

[76] Inventor: Frank O. Bastian, P.O. Box 976, Daphne, Ala. 36526

[21] Appl. No.: 09/050,585

[22] Filed: Mar. 30, 1998

[51] Int. Cl.[7] .......................... C12Q 1/68

[52] U.S. Cl. .......................... 435/6; 436/63; 436/518; 435/4; 435/7.32; 536/25.3

[58] Field of Search .......................... 436/63, 518; 435/4, 435/7.32, 6; 536/25.3

[56] References Cited

U.S. PATENT DOCUMENTS 5,693,467 12/1997 Roblin, III et al. .......................... 435/6

OTHER PUBLICATIONS

Deng et al. "Amplification of 16S rRNA Genes . . . " Jnl. of Micro. Methods 14 (1991) 53–61, 1991.

Otto et al., British Medical Journal 316(7131):577–582 (Feb. 21, 1998).

Zerr et al., Annals fo Neurology 43(1):32–40 (Jan. 1998).

Zerr et al., Lancet 348 (9031):846–849 (Sep. 28, 1996).

Hsich et al., New Engl J Med 335(13):924–930 (Sep. 26, 1996).

Schmerr and Jenny, Electrophoresis 19(3):409–414 (Mar. 1998).

Cooley et al., J Comparative Pathology 118(1):41–49 (Jan. 1998).

Schmerr et al., J Chromatography. B. Biomedical Sciences & Applications 697(1–2):223–229 (Sep. 12, 1997).

*Primary Examiner*—Kenneth R. Horlick
*Assistant Examiner*—Janell E. Taylor
*Attorney, Agent, or Firm*—Braman & Rogalskyj, LLP

[57] ABSTRACT

Provided is a method of detecting transmissible spongiform encephalopathies. The method comprises: selecting a sample from a subject to determine whether the subject has a transmissible spongiform encephalopathy; and detecting spiroplasma-specific 16S rDNA indicative of transmissible spongiform encephalopathies in the sample. The spiroplasma-specific 16S rDNA is preferably detected by contacting the sample with a pair of oligonucleotide primers under polymerase chain reaction conditions and detecting the resulting polymerase chain reaction product, wherein each of the pair of the oligonucleotide primers is complementary to spiroplasma-specific 16S rDNA indicative of transmissible spongiform encephalopathies. Further provided is an oligonucleotide having a nucleotide sequence complementary to spiroplasma-specific 16S rDNA indicative of transmissible spongiform encephalopathies; as well as an oligonucleotide having a nucleotide sequence specific to spiroplasma-specific 16S rDNA indicative of transmissible spongiform encephalopathies.

17 Claims, 3 Drawing Sheets

Spiroplasma mirum 16S ribosomal RNA small subunit (#M24662)(SEQ ID NO:7)

```
TAATACATAGGTGGCAAGCGTTATCCGGATTTATTGGGCGTAAAGCGTGCGCAGACGGTTTAGCAAGTTTGGGGTTAAAGACT
-5'-ACATAGGTGGCAAGCGTTATC-3'-----------------5'-GCGCAGACGGTTTAACAA-3'--------------
--- F-1 PRIMER (SEQ ID NO:1)------------------- F-2 PRIMER (SEQ ID NO:3)-----------
----------------------------------------------- GCGTAGGCGGTTTTGCAA (SEQ ID NO:8)---

GGGGCTCAACTCCAGTTCGCCTTGAAAACTGTTAGACTAGAGTGTAGGAGAGGTTGATGGAATTCCATGTGTAGCGGTGAAAT
-----------------------------------------------------------------------------------
-----------------------------------------------------------------------------------
-----------------------------------------------------------------------------------

GCGTAGATATATGGAGGAACACCAGTGGCGAAGGCGGTCAACTGGCCTATCACTGACGTTTAGG
--------- 3'-CTCCTTGTGGTCACCGCTT-5'-----------------------------
------------ R-2 PRIMER (SEQ ID NO:4)---------------------------
------------ GAAGAACACCTGTGGCGAA (SEQ ID NO:9)------------------

CACGAAAGCGTGGGGAGCAAATAGGATTAG—
3'-CTTTCGCATCCCTCGTTTATC-5'----
-- R-1 PRIMER (SEQ ID NO:2)----
-------------------------------
```

F-1 and R-1 external primers match specifically with mollicute 16S rDNA sequences but cannot be used to differentiate mycoplasma rDNA from spiroplasma rDNA.
F-2 and R-2 internal primers match spiroplasma rDNA sequences but show several mismatches at the 3' end of the mycoplasma rDNA sequences.
Sequence differences between mycoplasma and spiroplasma rDNA is shown below each internal primer sequence.

*FIG. 1*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

ACATAGGTGG CAAGCGTTAT C 21

(2) INFORMATION FOR SEQ ID NO:2:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:2:

CTATTTGCTC CCTACGCTTT C 21

(2) INFORMATION FOR SEQ ID NO:3:

(i) SEQUENCE CHARACTERISTICS:
(A) LENGTH: 18 base pairs
(B) TYPE: nucleic acid
(C) STRANDEDNESS: single
(D) TOPOLOGY: linear -continued (ii) MOLECULE TYPE: DNA (genomic)

(xi) SEQUENCE DESCRIPTION: SEQ ID NO:3:

GCGCAGACGG TTTAACAA 18

(2) INFORMATION FOR SEQ ID NO:4:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

TTCGCCACTG GTGTTCCTC 19

(2) INFORMATION FOR SEQ ID NO:5:

(i) SEQUENCE CHARACTERISTICS:
(A) LENGTH: 150 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

GCGCAGACGG TTTAGCAAGT TTGGGGTTAA AGACTGGGGC TCAACTCCAG TTCGCCTTGA 60

AAACTGTTAG ACTAGAGTGT AGGAGAGGTT GATGGAATTC CATGTGTAGC GGTGAAATGC 120

GTAGATATAT GGAGGAACAC CAGTGGCGAA 150

(2) INFORMATION FOR SEQ ID NO:6:

(i) SEQUENCE CHARACTERISTICS:
(A) LENGTH: 250 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

ACATAGGTGG CAAGCGTTAT CCGGATTTAT TGGGCGTAAA GCGTGCGCAG ACGGTTTAGC 60

AAGTTTGGGG TTAAAGACTG GGGCTCAACT CCAGTTCGCC TTGAAAACTG TTAGACTAGA 120

GTGTAGGAGA GGTTGATGGA ATTCCATGTG TAGCGGTGAA ATGCGTAGAT ATATGGAGGA 180

ACACCAGTGG CGAAGGCGGT CAACTGGCCT ATCACTGACG TTTAGGCACG AAAGCGTGGG 240

GAGCAAATAG 250

(2) INFORMATION FOR SEQ ID NO:7:

(i) SEQUENCE CHARACTERISTICS:
(A) LENGTH: 260 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

TAATACATAG GTGGCAAGCG TTATCCGGAT TTATTGGGCG TAAAGCGTGC GCAGACGGTT 60

-continued

```
TAGCAAGTTT GGGGTTAAAG ACTGGGGCTC AACTCCAGTT CGCCTTGAAA ACTGTTAGAC    120

TAGAGTGTAG GAGAGGTTGA TGGAATTCCA TGTGTAGCGG TGAAATGCGT AGATATATGG    180

AGGAACACCA GTGGCGAAGG CGGTCAACTG GCCTATCACT GACGTTTAGG CACGAAAGCG    240

TGGGGAGCAA ATAGGATTAG                                                260
```

(2) INFORMATION FOR SEQ ID NO:8:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

```
GCGTAGGCGG TTTTGCAA                                                   18
```

(2) INFORMATION FOR SEQ ID NO:9:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

```
GAAGAACACC TGTGGCGAA                                                  19
```

(2) INFORMATION FOR SEQ ID NO:10:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:10:

```
GAGGAACACC AGTGGCGAA                                                  19
```

(2) INFORMATION FOR SEQ ID NO:11:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

```
ACATAGGTGG CAAGCGTTAT C                                               21
```

(2) INFORMATION FOR SEQ ID NO:12:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

-continued

```
(xi) SEQUENCE DESCRIPTION: SEQ ID NO:12:

GCGCAGACGG TTTAGCAA                                       18


(2) INFORMATION FOR SEQ ID NO:13:

     (i) SEQUENCE CHARACTERISTICS:
          (A) LENGTH: 21 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:13:

GAAAGCGTGG GGAGCAAATA G                                   21
```

DETECTION OF TRANSMISSIBLE SPONGIFORM ENCEPHALOPATHIES

FIELD OF THE INVENTION

The subject invention is directed generally the detection of transmissible spongiform encephalopathies, and more particularly to a method of detecting transmissible spongiform encephalopathies (TSE) which utilizes a nested polymerase chain reaction for sensitive and specific detection of spiroplasma 16S rDNA in TSE.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

The recent outbreak of new variant cases of Creutzfeldt-Jakob disease (nvCJD) in Europe (Will et al. 1996) may signal the beginning of a major world health problem. NvCJD appears to have evolved from a concurrent epidemic of bovine spongiform encephalopathy (BSE) in English cattle (Brown et al. 1997). The root of the problem has been the endemic presence of scrapie in the large sheep population in Britain and the common practice of feeding sheep offal to cattle in the form of bone meal (Wilesmith et al. 1991). The indifference of scientists as to the likelihood of scrapie and subsequently BSE being potential human health risks directly led to the current threat of nvCJD in Britain. The problem is further compounded by the possibility of contamination of the blood supply by professional blood donors who eventually develop CJD, thereby providing a mechanism for even more widespread dissemination of the disease (FDA Committee 1994). It is, therefore, imperative to develop a pre-clinical screening test for the transmissible spongiform encephalopathies (TSE).

GENERAL BACKGROUND AND SIGNIFICANCE

A. The Disease

Creutzfeldt-Jakob disease (CJD), a rare disease with a world-wide occurrence, is characterized by rapidly progressive dementia, neurological deterioration, myoclonus and a triphasic encephalographic pattern (Brown et al. 1994). Ordinarily, CJD is a sporadic disease seen in an older population with a peak incidence (1–2 per million per year) at age 60 years. CJD is uniformly fatal with 90% of patients dying within one year. A rarer familial form of the disease (5% of CJD cases), is transmitted as an autosomal dominant. The histopathology of CJD is characterized by widespread spongiform alteration of gray matter, proliferation of hypertrophic astrocytes, and occasionally, focal tissue deposits with tinctorial properties of amyloid (15% of CJD cases, but consistently observed in familial CJD). Amyloid plaques surrounded by focal vacuolization of the neuropil are abundant in brain tissues from patients afflicted with the new variant of CJD (nvCJD) (Will et al. 1996). The nvCJD cases occurred in a youthful population (16 to 35 yrs) and are clinically distinctive from sporadic CJD cases in that they present with psychiatric symptoms and have a longer clinical course.

CJD is categorized as a transmissible spongiform encephalopathy (TSE), which has been long recognized in both domestic and wild animal populations as scrapie. Scrapie has occurred in sheep for over 200 years (Brown et al. 1994) and is endemic in many countries. The disease occurs in approximately one third of English flocks and has persisted in the United States in scattered flocks. Similar histopathology and clinical syndrome is seen in mink farm populations (Transmissible mink encephalopathy [TME]) and in cattle in England and in Europe (Bovine spongiform encephalopathy [BSE]). TSE in animals shows a variable distribution of lesions dependent upon the strain of the agent involved. Pathologic studies of experimental scrapie in mice have shown evidence of multiple strains whereas BSE in cattle or in experimental animals shows a uniform neuropathological pattern suggesting a singular TSE strain (Bruce et al. 1994). Amyloid deposition is not prevalent in scrapie in sheep but is abundant in some experimental scrapie mouse models. BSE has occurred in epidemic proportions since the disease was recognized in 1986 in English cattle (Wilesmith et al. 1991). BSE-infected animals have been banned from the human food chain since 1988.

BSE has been linked to the nvCJD human cases. The unique neuropathological pattern associated with nvCJD human cases has been seen in Macaques inoculated with the BSE agent (Lasmezas et al. 1996c). Furthermore, the pattern of binding of sugar moieties to $PrP^{res}$ (an infection-specific protease-resistant protein—see below) derived from nvCJD-infected humans and BSE-infected cattle shows distinctly different sugar binding properties compared to $PrP^{res}$ associated with sporadic human CJD (Collinge et al. 1996). The ability of the BSE agent to infect humans presumes an increased virulence of a transformed BSE agent (the nvCJD strain) which has likely evolved from the practice of feeding sheep offal to cattle; this is especially significant since experimental serial passage of the CJD agent in hamsters has resulted in adaptation or mutation of the agent with shortening of the incubation period from 467 days to 216.5 days (Manuelidis et al. 1976). In short, there has evolved a virulent CJD agent strain which has readily adapted to humans, thereby posing a serous threat of a future epidemic of the disease, possibly through our blood supply.

B. Transmission & Pathogenesis of the Disease

CJD was first recognized as a TSE in 1959 (Hadlow 1959) when a comparison was made between the pathology of scrapie and that of kuru (a fatal degenerative brain disease occurring among the Fore people of eastern New Guinea) and CJD, a worldwide rare degenerative human brain disease. Both kuru and CJD were subsequently passaged to chimpanzees (Gibbs et al. 1968). Since the Fore people practiced cannibalism, it was presumed to be caused by oral transmission. Subsequently, kuru was transmitted experimentally to nonhuman primates via the oral route (Gibbs et al. 1980). The persistence of scrapie infectivity in lymphoid tissues of sheep along the GI tract, including tonsils, supports the oral route as a significant portal of entry for the TSE agent/s (Kimberlin and Walker 1989).

The involvement of the reticuloendothelial system in the pathogenesis of TSE is significant. Following experimental inoculation of scrapie into rodents, the agent replicates in the spleen and shows a hematogenous phase before eventually localizing to the brain (Casaccia et al. 1989: Fraser and Dickinson 1978). Pathology is only evident in brain tissue although a depletion of B lymphocytes in the spleen has been seen (unpublished data). Tissues from scrapie or CJD infected animals, for the most part, show no evidence of a gross host inflammatory reaction (Bastian 1991), although there is significant microglial proliferation and T-lymphocyte recruitment in mouse scrapie-infected brains long before onset of clinical symptoms (Betmouni et al. 1996). The inefficiency of producing scrapie infection in the severe combined immunodeficiency mouse model shows the importance of the immune system in the pathogenesis of scrapie infection (Lasmezas et al. 1996*a*).

Very little is known about the hematogenous phase in TSE and, therefore, the degree of safety of our blood supply from contamination by the CJD transmissible agent is unknown (FDA Committee 1994). The CJD agent has been experimentally transmitted via blood inoculation into rodents (Manuelidis et al. 1985; Tateishi 1985). The possibility of accidental transmission of the disease through blood or blood products is real in light of previous history of iatrogenic transmission via necropsy tissues (Diringer and Braig 1989; Duffy et al. 1974) and contaminated surgical instruments (Bernoulli et al. 1977). In the 1980's, CJD followed therapeutic administration of growth hormone obtained from cadaveric pituitary glands, some cases with incubation periods of 8–11 years duration (Preece 1991). Therefore, the threat of contamination of blood makes it imperative that a screening method to circumvent exposure to the transmissible agent of CJD be devised.

C. Nature of the Agent

A few biological and physical properties of the TSE agent are known from TSE transmission experiments in rodents. The transmissible agents of scrapie and CJD are relatively large, i.e., the size of a medium size virus (>25 nanometers) (Dron and Manuelidis 1996) and TSE infectivity sediments on sucrose gradients primarily within the microsomal fraction (Tamai 1991). The TSE agents show marked resistance to radiation (Bockman 1991) although not necessarily out of the realm of a conventional virus (Rohwer 1984). The survival of the scrapie agent following exposure to high temperatures (Brown et al. 1982) is considered the most significant and unconventional property. However, 100° C. kills 99% of the scrapie agent in 1 minute (Rohwer 1984) with complete sterilization of scrapie-contaminated material by steam autoclaving at 132° C. for 60 minutes (Kimberlin et al. 1983) mimicking properties of thermophilic bacteria. Furthermore, only a small subpopulation of the agent shows this unusual resistance, a property not inconsistent with spore formation in bacteria.

The most often cited study suggesting that the TSE does not possess a nucleic acid component is the single report describing unusual resistance of the scrapie agent to psoralen and UV radiation (Bellinger-Kawahara et al. 1987). On the other hand, there is some question regarding the interpretation of that data since many viruses (i.e., polio) and spore forming bacteria (i.e., Bacillus subtilis) are resistant to the penetration of psoralen and therefore are not susceptible to the UV radiation (Personal communication, John Hearst, 1996). Indeed, biological properties of the transmissible agent, such as exponential replication, strain variation, and mutation, and long or evasive persistence in the host suggest that it possesses its own genome (Dron and Manuelidis 1996: Lasmezas et al. 1996*b*). In fact, no TSE infectivity has been demonstrable in preparations devoid of nucleic acids (Akowitz et al. 1994) and treatments that disrupt or solubilize nucleic acid-protein complexes destroy TSE infectivity (Manuelidis et al. 1995).

D. Search for a Marker of the Agent

An infection-associated protein or 'prion': A protease-resistant low molecular weight protein, $PrP^{res}$ and the product of its limited proteolysis, PrP 27–30 or prion (Prusiner et al. 1984), are demonstrated by Western blot of TSE brain homogenates after detergent extraction (DeArmond and Prusiner 1995). $PrP^{res}$ is produced from $PrP^{c}$, a normally occurring, protease sensitive host isoform encoded by a chromosomal gene (Oesch et al. 1985). Although $PrP^{c}$ and $PrP^{res}$ have identical molecular weights of 33 to 35 kd, $PrP^{c}$ is transformed to $PrP^{res}$ by a post-translational process occurring in the Golgi (Pan et al. 1993). $PrP^{res}$ then accumulates intracellularly in secondary lysosomes (McKinley et al. 1991). The transition to a prion involves significant conformational changes with acquisition of an increased β-sheet structure (Pan et al. 1993). The human PrP gene maps to the short arm of chromosome 20 (Goldfarb et al. 1994). $PrP^{c}$, found in all mammals, is a membrane protein that is bound to the external surface of cells by a glycolipid anchor (Stahl et al. 1987). The highest levels of PrP gene expression are found in neurons (Kretzschmar et al. 1986).

There is evidence that the prion is involved in the pathogenesis of the TSE's. Mice, in which the PrP gene has been ablated, when inoculated with scrapie, do not develop clinical or neuropathological features of scrapie nor do they propagate prions (Brandner et al. 1996). The PrP gene is important in determining the incubation period (Bruce et al. 1991) and transgenic experiments have shown that the level of PrP expression is inversely related to the incubation time (Prusiner et al. 1990). There are different patterns of PrP distribution in tissue sections from animals inoculated with different prion isolates as seen by immune histochemistry (DeArmond and Prusiner 1995). PrP, derived from different clinical forms of the disease, are digested into different size fragments by a protein-splitting enzyme suggesting strain-specific PrP conformational differences. The propagation of prions requires amino acid homology between the prion ($PrP^{res}$ ) and the $PrP^{c}$ of the host, and differences in homology may account for the host barrier (DeArmond and Prusiner 1995). Nevertheless, the proponents of the "prion" theory or protein-only hypothesis have postulated that there is need of cellular co-factors (i.e., protein X and/or protein Y; Y may be a nucleic acid—Personal communication, Telling, 1996) that recognizes some residues of the $PrP^{res}$ that are specific to the invading infectious agent (Telling et al. 1994). Protein X may be a chaperon-like molecule that forms a ternary complex with $PrP^{c}$ and $PrP^{res}$ and catalyzes the conversion of $PrP^{c}$ to $PrP^{res}$ (Edenhofer et al. 1996) thereby producing the infection. Such phenomena are proposed to occur spontaneously.

There is, however, a large body of data indicating that PrP itself is insufficient to transmit CJD. No infectivity is demonstrable with purified, recombinant or transgenic PrP protein (Riesner et al. 1996; Selvaggini et al. 1993). $PrP^{res}$ has been dissociated from infectivity (Riesner et al. 1996: Sakaguchi et al. 1993).

Amphotericin B treatment of hamsters infected with scrapie significantly delays buildup of $PrP^{res}$ but does not inhibit the increase in infectivity thereby appearing to dissociate the protein from infectivity (Xi et al. 1992). The absence of prion accumulation in brains in over 55% of mice inoculated with the BSE agent is highly suggestive that $PrP^{res}$ is a product of the infection rather than being the causal agent (Lasmezas et al. 1997). One explanation for the role of the prion in the TSE's is that the protein is an important receptor onto which the transmissible agent binds (Personal communication, P Brown, 1997). Dr. Brown suggested that a number of agents, including Spiroplasma, could be involved in the transmissibility of the disease but that the prion plays a very important role in the pathogenesis of the TSE's. It is apparent, at this time, that the role of the prion in the TSE's is not understood.

E. Spiroplasma or Mycoplasma as the Cause of CJD

Research points to a Mollicute (Spiroplasma or Mycoplasma), a class of cell wall-less prokaryotes, as the most likely candidate to be the causal agent of CJD. The Mycoplasmas are small pleomorphic organisms, consisting of coccoid or filamentous forms (Kenny 1985). Mycoplasmas have the smallest genome ($5 \times 10^8$ daltons) known for any free-living organism. Mycoplasmas are fastidious and require enriched medium containing peptone, yeast extract (source of preformed nucleic acid precursors) and animal serum (source of cholesterol). Several Mycoplasmas are associated with human disease, the best known being *Mycoplasma pneumoniae*. An AIDS-associated mycoplasma, related to *Mycoplasma fermentens*, has been discovered (Lo et al. 1989). None of the known Mycoplasma strains have been associated with a spongiform encephalopathy in mammals.

Spiroplasma are distinct from mycoplasma in possessing a helical morphology and being motile (Whitcomb 1980). They are present in the hemolymph of most insects, and abound in the salivary glands of vector insects that transmit plant diseases (Saglio and Whitcomb 1979). Spiroplasmas contain both DNA and RNA and possess all the machinery of protein synthesis. The genome size is $10^9$ daltons and the G+C content of its DNA is 26 mol% (Bove and Saillard 1979). Spiroplasma are fastidious, requiring enriched medium of high osmolality for growth (Tully et al. 1977). Although most Spiroplasmas known to exist by microscopic observation are not culturable, 26 serologically distinct groups have been grown in vitro (Abalain-Colloc et al. 1993). Spiroplasma of different strains show a great deal of biological diversity (Konai et al. 1996). Some strains show restricted growth over a small range in temperatures whereas other strains are capable of growth at temperatures ranging from 5° C. to 45° C. Spiroplasma produce deeply situated poorly defined fried-egg colonies on solid agar because of the mobility of the organism (Saglio and Whitcomb 1979; Whitcomb 1980). They show vigorous whirling and flexing movements in liquid culture and a helical morphology during at least a portion of their growth cycle in liquid or solid medium (Saglio and Whitcomb 1979). They also require exogenous cholesterol for growth.

In 1961, a Spiroplasma called Suckling mouse cataract agent (SMCA) was isolated from a pooled extract of rabbit ticks (Elizan et al. 1972). The agent was shown to grow to high titer in the eyes and brain of newborn mice, when inoculated intracerebrally (ic). Spiroplasmas have persisted in the mouse brain as long as 180 days and have been recovered as late as 2¼ years after inoculation (Clark and Rorke 1979). SMCA is irregularly present in the blood of infected mice between 1 hr and 18 days after inoculation but not thereafter. The GT-48 tick-derived Spiroplasma is more lethal and produces a severe encephalopathy in suckling rats (Bastian et al. 1984b)

In mice inoculated with SMCA, there is a prominent microcytic encephalitis localized to the subpial and subependymal zones and deep gray matter (Elizan et al. 1972). A mild mononuclear cell infiltrate may be present. There is prominent proliferation of astrocytes in some regions. The primary abnormality noted at 18 months after inoculation consists of a few multivacuolated neurons (Clark and Rorke 1979) which is characteristic of naturally occurring scrapie (Bastian 1991). Hydrocephalus is apparent in 36% of rats inoculated with SMCA (Elizan et al. 1972); hydrocephalus is also seen in experimental CJD infection in hamsters (Manuelidis et al. 1978) and experimental scrapie in mice (Pattison 1965). Similar spongiform encephalopathy in suckling rats inoculated with the GT-48 Spiroplasma has been reported (Bastian et al. 1984b) and the Spiroplasma has been shown to be neurotropic (Bastian et al. 1987b). French researchers subsequently showed that other Spiroplasma strains are capable of persistence and pathogenicity in mice, some able to multiply and survive for up to nine months with significant neurological symptoms (Humphery-Smith et al. 1992).

F. Significance

The potential contamination of our blood supply from professional blood donors who later developed CJD and the emergence of a new virulent vCJD agent has necessitated a priority to developing methodology for screening blood donors for CJD. Clinical diagnosis of CJD is in error in 25% of instances (Bastian 1991). Definitive diagnosis of these diseases can only be made by histologic examination of brains or PrP determinations of infected brain tissues (Ironside 1996). An immunoassay for 14-3-3 protein in spinal fluid (CSF) is positive in 96% of CJD cases, but is false-positive in Herpes encephalitis or following a recent stroke (Hsich et al. 1996). This CSF test becomes positive just prior to onset of clinical disease experimentally and is, therefore, of no practical value in developing a preclinical test for screening blood donors. Similarly, the prion has not been suitable for development of a preclinical test for the TSE's since it is a modified host protein and does not generate any antibody response (Prusiner 1996). Although the buildup of $PrP^{res}$ in the tissues is useful for diagnosis of autopsy or biopsy tissues, such examinations are not feasible for routine screening of animals, although biopsy of tonsil tissues has been proposed as a preclinical diagnostic tool (Vankeulen et al. 1996).

SUMMARY OF THE INVENTION

The emergence of a dangerous new variant of Creutzfeldt-Jakob Disease (CJD) in Europe has raised the urgent need for a pre-clinical test to eradicate the zoonotic reservoir of the disease and to screen blood donors to prevent dissemination of the transmissible agent. In accordance with the subject invention, the presence of spiroplasma 16S rDNA in brain tissues from CJD patients and scrapie-infected hamsters but not in controls has been demonstrated. The methodology of the subject invention therefore provides the basis for a pre-clinical test for this group of diseases.

More particularly, the subject invention provides a method of detecting transmissible spongiform encephalopathies. The method comprises: selecting a sample from a subject to determine whether the subject has a transmissible spongiform encephalopathy; and detecting spiroplasma-specific 16S rDNA indicative of transmissible spongiform encephalopathies in the sample. The spiroplasma-specific 16S rDNA is preferably detected by contacting the sample with a pair of oligonucleotide primers under polymerase chain reaction conditions and detecting the resulting polymerase chain reaction product, wherein each of the pair of the oligonucleotide primers is complementary to spiroplasma-specific 16S rDNA.

Further provided is an oligonucleotide having a nucleotide sequence complementary to the spiroplasma-specific 16S rDNA indicative of transmissible spongiform encephalopathies; as well as an oligonucleotide having a nucleotide sequence specific to spiroplasma-specific 16S rDNA indicative of transmissible spongiform encephalopathies.

BRIEF DESCRIPTION OF THE DRAWINGS

These and other features and advantages of this invention will be evident from the following detailed description of preferred embodiments when read in conjunction with the accompanying drawings in which:

FIG. 1 shows the *Spiroplasma mirum* 16S ribosomal RNA small subunit (GenBank Accession No. M24662)(SEQ ID NO:7) with primer sets developed according to the subject invention shown in bold print. F-1 (SEQ ID NO:1) and R-1 (SEQ ID NO:2) external primers match specifically with mollicute 16S rDNA sequences (SEQ ID NO:11 and SEQ ID NO:13, respectively) but cannot be used to differentiate mycoplasma rDNA from spiroplasma rDNA. F-2 (SEQ ID NO:3) and R-2 (SEQ ID NO:4) internal primers match spiroplasma rDNA sequences (SEQ ID NO:12 and SEQ ID NO:10, respectively) but show several mismatches at the 3' end of the mycoplasma rDNA sequences. Sequence differences between mycoplasma and spiroplasma rDNA are shown below each internal primer sequence (SEQ ID NO:8 for F-2 and SEQ ID NO:9 for R-2);

Figure 2:
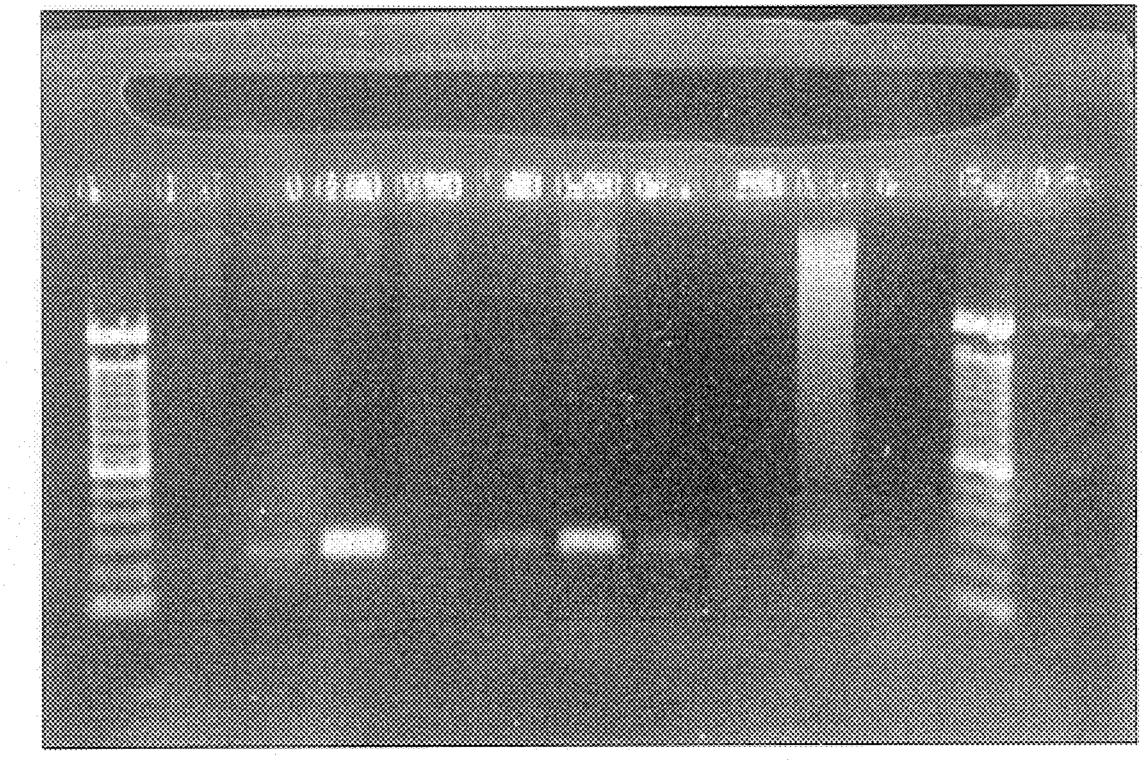
FIG. 2 illustrates a PCR study of CJD and Alzheimer disease brain samples using the external set of primers specific for mollicute 16S rDNA. The PCR study shows a 250 bp PCR product in all six CJD cases whereas DNA from two Alzheimer cases did not yield PCR product.
Figure 3:
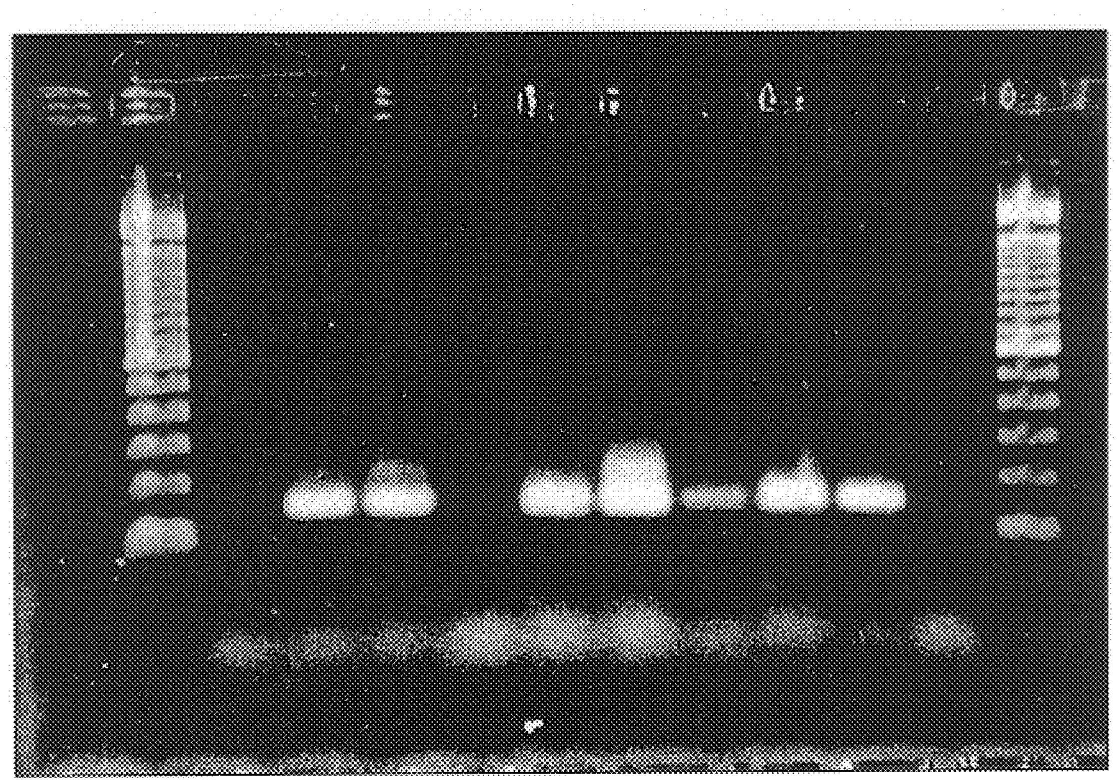
Figure 4:
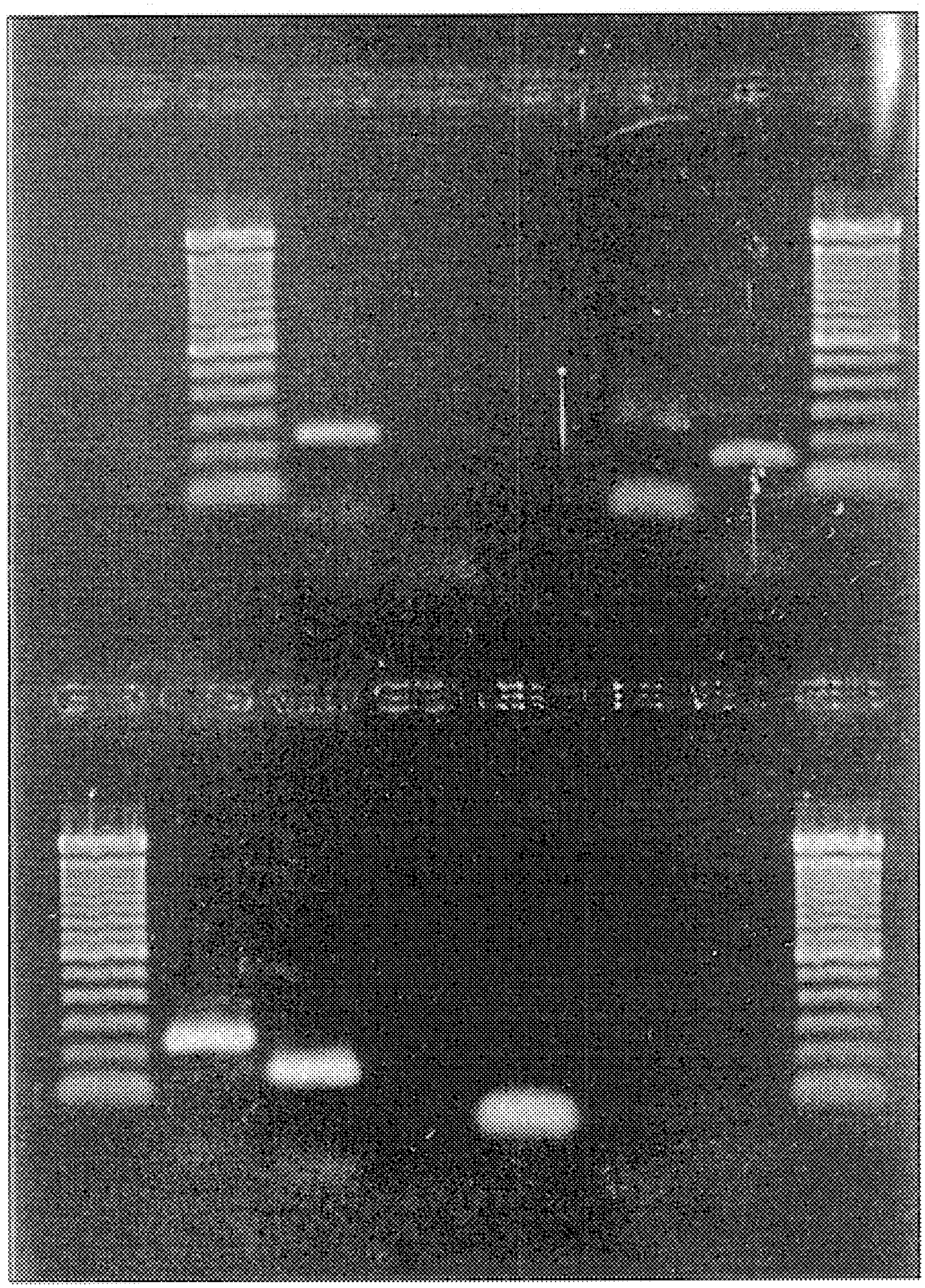

Lanes 1&12—DNA molecular weight markers; lanes 2&5—DNA from two Alzheimer disease cases; lanes 3,4, 6,7,8,9—DNA from six different CJD cases (DNA derived from formalin fixed tissues in lanes 7&8) ; lane 10—spiroplasma DNA; and no DNA template in lane 11;

FIG. 3 illustrates a nested PCR of CJD and Alzheimer disease brain DNA extracts shown in FIG. 2. This nested PCR reveals a spiroplasma-specific 150 bp 16S rDNA PCR product in only DNA derived from the CJD cases. Lanes 1&12—DNA molecular weight markers; lanes 2&5—Alzheimer disease DNA; lanes 3,4,6,7,8,9—CJD DNA; lane 10—spiroplasma DNA; and no DNA template in lane 11; and FIG. 4 illustrates a nested PCR of scrapie-infected and normal hamster brain samples using both external and internal primer sets. This nested PCR yielded a spiroplasma-specific 16S rDNA 150 bp PCR product only in DNA from the scrapie-infected brain sample and not in the normal hamster brain DNA. A mollicute-specific 16S rDNA 250 bp PCR product is present in both the normal and scrapie-infected hamster brain samples suggesting a concurrent mycoplasma infection in the normal pooled hamster brains. Upper tier, lanes 1&7—DNA molecular weight markers; normal hamster brain DNA with external primers (lane 2) and internal primers (lane 3); lane 4—empty; scrapie-infected hamster brain DNA with external primers (lane 5) and internal primers (lane 6); lower tier, lanes 8&15—DNA molecular weight markers; spiroplasma DNA with external (lane 9) and internal primers (lane 10); lane 11—empty; no DNA template PCR product (from first PCR) with external primers (lane 12) and internal primers (lane 13) primers; lane 14—no DNA template. Note primer dimer artifact in lane 12.

DETAILED DESCRIPTION OF THE INVENTION

The invention provides a method of detecting transmissible spongiform encephalopathies. The method comprises selecting a sample from a subject to determine whether the subject has a transmissible spongiform encephalopathy, and detecting spiroplasma-specific 16S rDNA indicative of transmissible spongiform encephalopathies in the sample.

As used herein transmissible spongiform encephalopathies (TSEs) include all forms of TSEs recognized in the art (and those yet to be discovered). Creutzfeldt-Jakob disease (CJD) is the TSE found in humans. Bovine spongiform encephalopathy (BSE) is the TSE found in bovine animals (cattle). Scrapie is the TSE found in sheep. Additional discussion of TSEs can be found in the background above. Any subject susceptible to TSE can be examined according to the method of the subject invention. Such subjects include humans (CJD), cattle (BSE), and sheep (scrapie), to illustrate just a few of the most common subjects.

The method of the subject invention detects spiroplasma-specific 16S rDNA that is indicative of TSE. Therefore, suitable samples include any samples in which the spiroplasma-specific 16S rDNA may be present. Such samples include, for example, tissue samples (brain, spleen, etc.)(removed from deceased subjects or biopsied from living subjects), bodily fluid samples (such as cerebral spinal fluid), and peripheral blood.

In a presently preferred embodiment, detecting the spiroplasma-specific 16S rDNA comprises contacting the sample with a pair of oligonucleotide primers under polymerase chain reaction conditions and detecting the resulting polymerase chain reaction product, wherein each of the pair of the oligonucleotide primers is complementary to spiroplasma-specific 16S rDNA indicative of TSE. An example of a pair of oligonucleotide primers are those primers having the nucleotide sequences as shown in SEQ ID NO:1 and SEQ ID NO:2. These oligonucleotide primers lead to a polymerase chain reaction product having about 250 base pairs. Another example of a pair of oligonucleotide primers are those primers having the nucleotide sequences as shown in SEQ ID NO:3 and SEQ ID NO:4. These oligonucleotide primers lead to a polymerase chain reaction product having about 150 base pairs.

In a presently preferred embodiment of the subject invention, nested PCR is used to specifically and sensitively detect even a single spiroplasma organism (thereby indicating TSE). In nested PCR, the sample is first contacted with a pair of oligonucleotide primers complementary to spiroplasma-specific 16S rDNA indicative of TSE under polymerase chain reaction conditions to generate a first polymerase chain reaction product (this can be accomplished using those primers having the nucleotide sequences as shown in SEQ ID NO:1 and SEQ ID NO:2 to generate a first PCR product having about 250 bp). A second PCR is then run using a second pair of oligonucleotide primers complementary to spiroplasma-specific 16S rDNA indicative of TSE, with the first PCR product as the sample (this can be accomplished using those primers having the nucleotide sequences as shown in SEQ ID NO:3 and SEQ ID NO:4 to generate a second PCR product having about 150 bp).

The invention further provides an oligonucleotide having a nucleotide sequence complementary to the spiroplasma-specific 16S rDNA indicative of transmissible spongiform encephalopathies. Oligonucleotides having a nucleotide sequence selected from the group consisting of SEQ ID NO:1, SEQ ID NO:2, SEQ ID NO:3, and SEQ ID NO:4 are examples of oligonucleotides as claimed herein.

The invention further provides an oligonucleotide having a nucleotide sequence specific to spiroplasma-specific 16S rDNA indicative of transmissible spongiform encephalopathies. The oligonucleotide having the nucleotide sequence as shown in SEQ ID NO:5 is an example of such an oligonucleotide as claimed herein.

In the following examples, Examples I-V provide the data supporting a role for a Spiroplasma species in the etiology of CJD. Example VI provides the data supporting the detection of transmissible spongiform encephalopathies by detecting spiroplasma-specific 16S rDNA indicative of TSE in a sample, as well as the data supporting the oligonucleotides as claimed herein.

EXAMPLE I

Discovery of a Spiroplasma-Like Organelle in Infected Brain Samples

We first became interested in exploring a more conventional microbial etiology for CJD upon discovering a peculiar spiral-shaped organelle present in neuronal cell processes in a CJD brain biopsy (Bastian 1979). These structures have not been found in normal brain tissue samples. This observation was later confirmed by us (Bastian et al. 1981) and others (Gray et al. 1980; Reyes and Hoenig 1981). The morphology of this organelle was reminiscent of Spiroplasma, a cell wall-less microorganism related to Mycoplasma but exhibiting a spiral cellular morphology (Whitcomb 1980). We have observed Spiroplasma by electron microscopy in the size range of the transmissible agent in broth cultures throughout the growth cycle.

EXAMPLE II

Spiroplasma Causes CJD-Like Pathology in Rats

We initially tested the hypothesis that Spiroplasma might cause a degenerative brain disorder in a rat model similar to TSE (Bastian et al. 1984b). *Spiroplasma mirum* strain, GT-48, was used for these experiments. We found that 30 to 300 organisms injected intracranially into suckling rats multiplied to a cell density of 106 CFUs per gram tissue within two weeks of infection. Although the incubation period for experimental Spiroplasma infection was significantly shorter than experimental TSE infection, the microcytic changes in the rat brain closely resembled the spongiform alteration of TSE. Electron micrographs of Spiroplasma-infected brain tissues were essentially identical to the pathology seen in CJD (Bastian 1991). Vacuolization without inflammation was seen in longstanding disease (8 weeks in this study). In our study, Spiroplasma were demonstrated by immunocytochemistry to localize to neurons and gray matter. Spiroplasma were clearly evident as spiral-shaped organisms in the diseased tissue at two weeks but were less obvious at eight weeks. It is noteworthy that even at eight weeks we were able to cultivate GT-48 Spiroplasma from the brains of these animals.

EXAMPLE III

Scrapie-Associated Fibrils are Morphologically Identical to Spiroplasma Fibril Proteins A characteristic and diagnostic feature of CJD and scrapie is the presence of fibrils in homogenized/protease-treated brain tissues (Merz et al. 1981; Merz et al. 1983). These fibrils are composed of two or four helically wound 4 nm subfilaments with straight segments 200 nm in length and possess a 10 nm periodicity. These structures, designated scrapie-associated fibrils (SAF) since they were first described in experimental scrapie (Merz et al. 1981), are distinctive from the usual twisted amyloid fibrils and, even though they are protease resistant, are not composed of PrP (Prusiner 1996). The term SAF has been inappropriately used as a synonym for prion rods, leading to the assumption that SAF are composed of PrP. However, because SAF accumulates in tissues in direct proportion to infectivity (Rubenstein et al. 1991), one might suspect it represents a part of the infectious agent. Several investigators, including ourselves, have identified fibrils in Spiroplasma that appear morphologically identical to SAF (Bastian et al. 1987a; Bastian et al. 1984a; Williamson 1974). The Spiroplasma fibrils were demonstrated in our studies to be protease resistant (Bastian et al. 1987a). McGarrity and colleagues have also reported protease-resistant proteins in several Mycoplasmas (Butler et al. 1991).

EXAMPLE IV

Protease-Resistant Spiroplasma Proteins Cross-React With Anti-Scrapie Antibody

Additional evidence connecting Spiroplasma to prion diseases involves the use of anti-scrapie antibody to probe Spiroplasma mirum proteins by Western blot analysis (Bastian et al. 1987a). The anti-scrapie polyclonal antisera was raised against protease-resistant proteins (including prion proteins) from scrapie strain ME7 infected mouse brains (Courtesy-Richard Rubenstein). This antisera was tested against a protease-resistant extract of *Spiroplasma mirum* grown in vitro. Four Spiroplasma protein bands reacted with this antisera, indicating that there is at least one protease-resistant protein in scrapie brains that cross-reacts with several Spiroplasma protease-resistant proteins. One interpretation of these results is that Spiroplasma antigens are present in the scrapie tissues.

EXAMPLE V

CJD Brain Extracts Contain Mollicute 16S Ribosomal RNA Gene Sequences

A recent and more compelling piece of evidence supporting a Spiroplasma etiology for CJD was the discovery, through PCR analysis, of Mollicute 16S ribosomal RNA gene sequences in CJD brain samples. For this study we designed two oligonucleotides suitable for PCR analysis from conserved sequences present in Spiroplasma and Mycoplasma 16S rRNA genes. These primers amplify a 1 kb fragment from both Mycoplasma and Spiroplasma DNA preparations.

Because 16S rRNA sequences are well conserved among related microorganisms, we predicted that they should amplify the relevant portions of genes encoding 16S rRNA from many strains of Spiroplasma, Mycoplasma or other phylogenetically related Mollicutes. Thus, these primers were used to screen CJD brain extracts for the presence of Mollicute 16S rDNA sequences. Even though only a limited number of samples were screened, a 1 kb fragment was successfully amplified from two CJD samples but not from controls. The 1 kb PCR product from Spiroplasma hybridized on Southern blot with Spiroplasma DNA, Mycoplasma DNA, and DNA from two CJD cases, but not with DNA from Alzheimer brain. The 1 kb product amplified from CJD brain sample was subsequently cloned and 300 base pairs sequenced. A DNA homology search using the GenBank database revealed the cloned sequence exhibited 95 to 97% homology to Mycoplasma and Spiroplasma 16S rRNA genes. Clearly, Mollicute DNA was present in those samples.

EXAMPLE VI

Detection of Spiroplasma-Specific 16S rDNA Indicative of TSE

Since Our Laboratory has compiled evidence over the past 25 years that a cell-wall-less bacterium is associated with the disease (Bastian 1979; Bastian 1991; Bastian et al. 1987a; Bastian et al. 1987b; Bastian et al. 1984b), we set out to determine if there is spiroplasma-related 16S rDNA in TSE tissues. The rationale for this approach is based on the fact that bacterial ribosomal genes tend to be conserved within a particular genus. We undertook, in this study, to search for spiroplasma-specific 16S rDNA in CJD and scrapie-infected tissues using the sensitive polymerase chain reaction (PCR).

For the PCR study, we selected oligonucleotide primers based upon available mollicute 16S rDNA sequences (SEQ ID NO:7). One set of primers (SEQ ID NO:1 and SEQ ID NO:2) was designed to produce a 250 bp PCR product (SEQ ID NO:6), which, although specific for mollicutes, could not differentiate between mycoplasma and spiroplasma. A second set of primers (SEQ ID NO:3 and SEQ ID NO:4) unique to spiroplasma was selected within the amplified region that produced a 150 bp PCR product (SEQ ID NO:5). This internal primer pair showed several mismatches with mycoplasma 16S rDNA, especially near the 3' ends. When used in succession with the external primers in nested PCR, the internal primer set became an extremely sensitive and specific method for detecting spiroplasma 16S rDNA. The primer sets and strategies are detailed in FIG. 1. In addition, the quality of the DNA from the human DNA samples was tested with a chromosome 17-specific primer pair (Becker et al. 1996).

PCR was carried out on DNA extracted from Spiroplasma mirum broth culture, from frozen and formalin fixed CJD brain tissues and from non-related frozen brain tissues, obtained at autopsy, primarily from Alzheimer disease patients. Other control samples included DNA from human lymph node, and from human lymphocyte preparations. Studies were carried out in a newly acquired laboratory wherein no prior work with spiroplasma had been done. DNA samples were freshly prepared using a QIAamp Tissue Kit (Qiagen Inc., Santa Clarita, Calif.). In addition, DNA derived from pooled hamster brains, one group infected with scrapie and another group from normal hamsters, was sent to us, courtesy of Dr. Robert Rohwer, Baltimore, Md. The standard PCR study was carried out using a MJ Research thermocycler programmed to 30 cycles with a 30 sec annealing time at 55° C. PCR reaction mixtures were prepared in a laboratory physically separate from other laboratories where the DNA was extracted or where the thermocycler was located. Ultrapure autoclaved distilled water was used for sample preparation. Pipetters were placed under UV light prior to use and filtered pipette tips and gloves (with frequent changes) were used for all steps in the study.

Direct sequencing of the PCR product from one case of CJD was carried out for comparison to known mollicute 16S rDNA sequences. Multiple PCR runs using the external primer set were done on DNA derived from one previously strongly positive case of Creutzfeldt-Jakob disease (see FIG. 2, lane 4). The combined PCR products from this case were electrophoresed in a large well on a 2% agarose gel. The 250 bp PCR product band was identified by long wave UV and cut out of the gel. DNA was extracted from this gel sample using a Qiagen kit (see above) with an efficiency of 250 ug/ul, as determined by spectrophotometer readings. The extracted 250 bp PCR product DNA was then submitted to a central laboratory for automated sequencing. In addition, a sample of the extracted 250 bp PCR product DNA was rerun by PCR using the internal set of primers. The resultant 150 bp PCR product was submitted as well to the central laboratory for automated sequencing.

PCR, using the external set of primers, yielded mollicute-specific 250 bp PCR product in DNA extracted from seven neuropathologically confirmed CJD cases. Data presented in FIG. 2 show positive findings in six of the CJD cases while no PCR product was visible in DNA extracts from two Alzheimer disease cases. Nested PCR of these samples yielded the spiroplasma-specific 150 bp PCR product in all of the CJD specimens and not in Alzheimer disease controls (FIG. 3). All of the brain-derived DNA from these samples were positive with the genomic DNA probe except for CJD cases #5 & #6 wherein the DNA, which had been extracted from formalin-fixed tissues, appeared to be significantly degraded. An additional 4 CJD cases were positive for spiroplasma DNA by nested PCR while showing no PCR product on the initial PCR using the external primers (PCR data not shown). The most likely explanation is that there are small numbers of microbes in these CJD specimens. A total of nine controls examined in these studies (three frozen Alzheimer diseased brains, two normal human brain samples, a human lymph node, and three human lymphocyte preparations) yielded no PCR product to the spiroplasma 16S rDNA probe. All of the human DNA control samples tested with the human genomic DNA probe showed intact DNA. A summary of the data is presented diagrammatically in Table 1.

The direct sequencing of both the 250 bp and 150 bp PCR products from one CJD case showed 92.5% homology with the Spiroplasma 16S rDNA. Comparison of the DNA sequence of the PCR product from the CJD case with mycoplasma 16S rDNA revealed 38 to 40 mismatches, representing 81% homology. These data indicate that a spiroplasma 16S RNA gene was clearly being amplified in the human DNA sample.

A nested PCR study of the samples sent by Dr. Rohwer revealed the spiroplasma-specific 150 bp PCR product in the DNA extracted from scrapie-infected hamster brain and not in the controls (FIG. 4). The mollicute-specific 250 bp PCR product, as seen in the normal hamster DNA preparation, may represent the presence of an associated mycoplasma infection or a contaminant. It is noteworthy that the nested PCR study was negative in the control hamster DNA for the 150 bp PCR product confirming that spiroplasma-specific 16S rDNA is only associated with the scrapie-infected hamster tissues. Also depicted in FIG. 4 is an important control wherein nested PCR was done on "no template DNA sample" from the prior PCR study resulting in no PCR product, thereby ruling out any occurrence of contamination during the procedure. The data gleaned from the experimentally scrapie-infected hamster brains sent by Dr. Rohwer are especially significant since the hamster DNA samples were extracted at another institution negating any possibility of contamination with spiroplasma during preparation of the hamster DNA extracts.

The consistent finding of spiroplasma-specific 16S rDNA in TSE tissues and not in controls, as shown in this study, represents the basis for a screening test. Currently, there is no reliable pre-clinical detection method for TSE. The immunoblot 14-3-3 protein detection method, developed by Harrington for screening cerebral spinal fluid (CSF), is subject to false positives when done in the clinical setting of recent stroke or Herpes encephalitis and the test is positive in CJD patients only after onset of clinical symptoms (Hsich et al. 1996). $PrP^{res}$ testing is only applicable to postmortem or biopsy tissues and the value of a new monoclonal antibody method for detection of abnormal PrP (Korth et al. 1997) may have limited application since $PrP^{res}$ accumulation is not a consistent finding in TSE (Lasmezas et al. 1997).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

| | Transmissible Spongiform Encephalopathy DNA | | | | | | | | | | | | Control DNA | | | | | | | | | | |
|---|---|---|---|---|---|---|---|---|---|---|---|---|---|---|---|---|---|---|---|---|---|---|---|
| PCR | DNA from Frozen or Fixed CJD Brains | | | | | | | | | | | Scr | S | Alz Br | | | H Br | | H LN | H Lymph | | | Ham |
| Method | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| External Primer Pair | + | + | + | + | + | + | + | − | − | − | − | + | + | − | − | − | − | − | − | − | − | − | + |
| Nested PCR | + | + | + | + | + | + | nd | + | + | + | + | + | + | − | − | − | nd | nd | nd | nd | nd | nd | − |
| Human Genomic Primer Pair | + | + | + | + | − | − | nd | + | + | + | + | nd | − | + | nd | + | + | + | + | + | + | + | nd |

CJD - Creutzfeld-Jakob Disease Brain DNA, 1 through 11
Scr - Scrapie Hamster Brain DNA, 12
S - Spiroplasma Broth Culture DNA, 13
Alz Br - Alzheimer Disease Brain DNA, 14, 15, and 16
H Br - Human Brain DNA, 17 and 18
H LN - Human Lymph Node DNA, 19
H Lymph - Human Blood Lymphocytes DNA, 20, 21, and 22
Ham - Normal Hamster Brain DNA, 23

REFERENCES

Abalain-Colloc, M. L., et al. 1993. International Journal of Systematic Bacteriology. 43:342–346.

Akowitz, A., et al. 1994. Nucleic Acids. Res. 22:1101–1107.

Bastian, F. O. 1979. Arch. Pathol. Lab. Med. 103:665–669.

Bastian, F. O. 1991. Neuropathology, 65–96. In Bastian, F. O. (ed.), Creutzfeldt-Jakob disease and other tranmissible spongiform encephalopthies. Mosby/YearBook, Baltimore, Md.

Bastian, F. O., et al. 1981. Lancet. 8:660.

Bastian, F. O., et al. 1987a. J. Clin. Microbiol. 25:2430–2431.

Bastian, F. O., et al. 1987b. Ann. Microbiol. 138:651–655.

Bastian, F. O., et al. 1984a. J. Neuropathol. Exp. Neurol. 43:333.

Bastian, F. O., et al. 1984b. Am. J. Pathol. 114:496–514.

Becker, S. A., et al. 1996. Cancer Res. 56:5092–5097.

Bellinger-Kawahara, C., et al. 1987. Virol. 160:271–274.

Bernoulli, C., et al. 1977. Lancet. 1:478–479.

Betmouni, S., et al. 1996. Neuroscience. 74:1–5.

Bockman, J. M. 1991. Physicochemical and biological properties of the transmissible agent, 11–35. In Bastian, F. O. (ed.), Creutzfeldt-Jakob disease and other transmissible spongiform encephalopathies. Mosby/YearBook, Baltimore, Md.

Bové, J. M., and C. Saillard. 1979. Cell biology of spiroplasmas, 83–153. In Whitcomb, R. F., and J. G. Tully (eds.), The mycoplasmas. Academic Press, New York, N.Y.

Brandner, S., et al. 1996. Nature. 379:339–343.

Brown, K. L., et al. 1997. J. Gen. Virol. 78:2707–2710.

Brown, P. M. D., et al. 1994. Ann. Neurol. 35:513–529.

Brown, P., et al. 1982. J. Inf. Dis. 145:683–687.

Bruce, M. E., et al. 1994. Phil Trans R Soc Lond B. 343:405–411.

Bruce, M. E., et al. 1991. J. Gen. Virol. 72:595–603.

Butler, G. H., et al. 1991. Infect. Immun. 59:1037–1042.

Casaccia, P., et al. 1989. Arch. Virol. 108:145–149.

Clark, H. F., and L. B. Rorke. 1979. Spiroplasmas of tick origin and their pathogenicity, 155–174. In Whitcomb, R. F., and J. G. Tully (eds.), The mycoplasmas. Academic Press, New York, N.Y.

Collinge, J., et al. 1996. Nature. 383:685–690.

DeArmond, S. J., and S. B. Prusiner. 1995. Am. J. Pathol. 146:785–811.

Diringer, H., and H. R. Braig. 1989. Lancet. 1:439–440.

Dron, M., and L. Manuelidis. 1996. Journal of NeuroVirology. 2:240–248.

Duffy, P., et al. 1974. N. Engl. J. Med. 290:692.

Edenhofer, F., et al. 1996. J. Virol. 70:4724–4728.

Elizan, T. S., et al. 1972. Proc. Soc. Exp. Biol. Med. 139:51–55.

FDA committee. 1994. FDA committee recommends some blood recalls for rare neurological disease, 1–4. In: Report of December 15–16 meeting of the Food and Drug Administration's Blood Products Advisory Committee. CCBC Newsletter, December 23/30.

Fraser, H., and A. G. Dickinson. 1978. J Comp Pathol. :563–573.

Gibbs, C. J., Jr., et al. 1980. J. Inf. Dis. 142:205–208.

Gibbs, C. J., Jr., et al. 1968. Science. 161:388–389.

Goldfarb, L. G., et al. 1994. Mol. Neurobiol. 8:89–97.

Gray, A., et al. 1980. Lancet. 2:152.

Hadlow, W. J. 1959. Lancet. 2:289–290.

Hsich, G., et al. 1996. N. Engl. J. Med. 335:924–930.

Humphery-Smith, I., et al. 1992. Med. J. Australia. 156:142.

Ironside, J. W., 1996. Neuropathological Diagnosis of Human Prion Disease: Morphological Studies, 35. In Baker, H., F, and R. Ridley M (eds.), Prion Diseases. Humana Press, Totowa, N.J.

Kenny, G. E. 1985. Mycoplasmas, 407–411. In Balorus, A., W. J. Hausler Jr., and H. J. Shadomy (eds.), Manual of clinical microbiology. ASM, Washington, D.C.

Kimberlin, R. H., and C. A. Walker. 1989. Virus Res. 12:213–220.

Kimberlin, R. H., et al. 1983. J. Neurol. Sci. 59:355–369.

Konai, M., et al. 1996. Curr. Microbial. 32:314–319.

Korth, C ., et al. 1997. Nature 390:74–77.

Kretzschmar, H. A., et al. 1986. Am. J. Pathol. 122:1–5.

Lasmézas, C. I., et al. 1996a. J. Viral. 70:1292–1295.

Lasmézas, C. I., et al. 1996b. J. Gen. Viral. 77:1601–1609.

Lasmézas, C. I ., et al. 1996c. Nature. 381:743–744.

Lasmezas, C. I., et al. 1997. Science. 275:402–405.

Lo, S.-C., et al. 1989. Am J Trop Med Hyg. 41:601–616 (89–164).

Manuelidis, E. E., et al. 1978. Nature. 271:778–779.

Manuelidis, E. E., et al. 1976. Proc. Natl. Acad. Sci. U.S.A. 73:223–227.
Manuelidis, E. E., et al. 1985. Lancet. :896–897.
Manuelidis, L., et al. 1995. Proc. Natl. Acad. Sci. U.S.A. 92:5124–5128.
McKinley, M. P., et al. 1991. Lab. Invest. 65:622–630.
Merz, P. A., et al. 1981. Acta Neuropathol. 54:63–74.
Merz, P. A., et al. 1983. Nature. 306:474–476.
Oesch, B., et al. 1985. Cell. 40:735–746.
Pan, K.-M., et al. 1993. Proc. Natl. Acad. Sci. U.S.A. 90:10962–10966.
Pattison, I. H. 1965. Experiments with scrapie with special reference to the nature of the agent and the pathology of the disease, 249–257. In Gajdusek, D. C., J. Gibbs C J, and M. Alpers (eds.), Slow, latent and temperate virus infections. U.S. Department of Health, Education and Welfare, Washington, D.C.
Preece, M. A. 1991. Clinical Endocrinology. 34:527–529.
Prusiner, S. B. 1996. Prions, 1245–1294. In Fields, B. N., D. M. Knipe, and P. M. Howley (eds.), Fundamental virology. Lippincott-Raven Publishers, Philadelphia, Pa.
Prusiner, S. B., et al. 1984. Cell. 38:127–134.
Prusiner, S. B., et al. 1990. Cell. 63:673–686.
Reyes, J. M., and E. M. Hoenig. 1981. J. Neuropathol. Exp. Neurol. 40:1–8.
Riesner, D., et al. 1996. J. Virol. 70:1714–1722.
Rohwer, R. G. 1984. Nature. 308:658–662.
Rubenstein, R., et al. 1991. J. Inf. Dis. 164:29–35.
Saglio, P. H. M., and R. F. Whitcomb. 1979. Diversity of wall-less prokaryotes in plant vascular tissue, fungi, and invertebrate animals, 1–36. In Whitcomb, R. F., and J. G. Tully (eds.), The mycoplasmas. Academic Press, New York, N.Y.
Sakaguchi, S., et al. 1993. J. Gen. Virol. 74:2117–2123.
Selvaggini, C., et al. 1993. Biochem Biophys Acta. 194:1380–1386.
Stahl, N., et al. 1987. Cell. 51:229–240.
Tamai, Y. 1991. Neurochemistry, 97–114. In Creutzfeldt-Jakob disease and other transmussible spongiform encephalopathies. Mosby/YearBook, Baltimore, Md.
Tateishi, J. 1985. Lancet. 2:1074.
Telling, G. C., et al. 1994. Proc. Natl. Acad. Sci. U.S.A. 91:9936–9940.
Tully, J. G., et al. 1977. Science. 195:892–894.
Vankeulen, L. J. M., et al. 1996. J. Clin. Microbiol. 34:1228–1231.
Whitcomb, R. F. 1980. Annu. Rev. Microbiol. 34:677–709.
Wilesmith, J. W., et al. 1991. Vet. Rec. 128:199–203.
Will, R. G., et al. 1996. Lancet. 347:921–925.
Williamson, D. L. 1974. J. Bacteriol. 117:904–906.
Wisniewski, H. M., et al. 1996. Lancet. 347:1114.
Xi, Y. G., et al. 1992. Nature. 356:598–599.

What is claimed is:

1. A method of detecting transmissible spongiform encephalopathies, the method comprising:

selecting a sample from a subject to determine whether the subject has a transmissible spongiform encephalopathy; and detecting spiroplasma-specific 16S rDNA indicative of transmissible spongiform encephalopathies in the sample thereby detecting transmissible spongiform encephalopathies.

2. The method of claim 1 wherein the transmissible spongiform encephalopathy is Creutzfeldt-Jakob disease and the subject is a human.

3. The method of claim 1 wherein the transmissible spongiform encephalopathy is bovine spongiform encephalopathy and the subject is a bovine animal.

4. The method of claim 1 wherein the transmissible spongiform encephalopathy is scrapie and the subject is a sheep.

5. The method of claim 1 wherein the sample is a tissue sample.

6. The method of claim 5 wherein the tissue sample is a brain tissue sample.

7. The method of claim 6 wherein the brain tissue sample is a biopsied sample from the brain.

8. The method of claim 1 wherein the sample is a body fluid.

9. The method of claim 8 wherein the body fluid is cerebral spinal fluid.

10. The method of claim 1 wherein the sample is peripheral blood.

11. The method of claim 1 wherein detecting the spiroplasma-specific 16S rDNA comprises contacting the sample with a pair of oligonucleotide primers under polymerase chain reaction conditions and detecting the resulting polymerase chain reaction product, wherein each of the pair of the oligonucleotide primers is complementary to spiroplasma-specific 16S rDNA indicative of transmissible spongiform encephalopathies.

12. The method of claim 11 wherein the pair of oligonucleotide primers have the nucleotide sequences as shown in SEQ ID NO:1 and SEQ ID NO:2 and wherein the resulting polymerase chain reaction product has about 250 base pairs.

13. The method of claim 11 wherein the pair of oligonucleotide primers have the nucleotide sequences as shown in SEQ ID No:3 and SEQ ID NO:4 and wherein the resulting polymerase chain reaction product has about 150 base pairs.

14. The method of claim 11 further comprising contacting the polymerase chain reaction product with a second pair of oligonucleotide primers under polymerase chain reaction conditions and detecting the second resulting polymerase chain reaction product, wherein each of the second pair of the oligonucleotide primers is complementary to spiroplasma-specific 16S rDNA indicative of transmissible spongiform encephalopathies.

15. The method of claim 14 wherein the pair of oligonucleotide primers have the nucleotide sequences as shown in SEQ ID NO:1 and SEQ ID NO:2, wherein the resulting polymerase chain reaction product has about 250 base pairs, wherein the second pair of oligonucleotide primers have the nucleotide sequences as shown in SEQ ID NO:3 and SEQ ID NO:4, and wherein the second resulting polymerase chain reaction product has about 150 base pairs.

16. An oligonucleotide having a nucleotide sequence complementary to spiroplasma-specific 16S rDNA indicative of transmissible spongiform encephalopathies and selected from the group consisting of SEQ ID NO:1, SEQ ID NO:2, SEQ ID NO:3, and SEQ ID NO:4.

17. An oligonucleotide having a nucleotide sequence specific to spiroplasma-specific 16S rDNA indicative of transmissible spongiform encephalopathies and as shown in SEQ ID NO:5.

* * * * *